United States Patent [19]

Freund et al.

[11] 4,264,814
[45] Apr. 28, 1981

[54] METHOD FOR DETECTING TRACE IMPURITIES IN GASES

[75] Inventors: Samuel M. Freund, Santa Fe; William B. Maier, II, Los Alamos; Redus F. Holland, Los Alamos; Willard H. Beattie, Los Alamos, all of N. Mex.

[73] Assignee: The United States of America as represented by the United States Department of Energy, Washington, D.C.

[21] Appl. No.: 62,372

[22] Filed: Jul. 31, 1979

[51] Int. Cl.³ .................. G01N 31/00; G01N 33/00
[52] U.S. Cl. .................................................. 250/304
[58] Field of Search ............. 250/304; 356/36; 73/23

[56] References Cited

U.S. PATENT DOCUMENTS 2,917,629  12/1959  Andrychuk .......................... 250/304
3,530,292  9/1970  Hill ....................................... 250/304

*Primary Examiner*—Bruce C. Anderson
*Attorney, Agent, or Firm*—Paul D. Gaetjens; Richard G. Besha; James E. Denny

[57] ABSTRACT

A technique for considerably improving the sensitivity and specificity of infrared spectrometry as applied to quantitative determination of trace impurities in various carrier or solvent gases is presented. A gas to be examined for impurities is liquefied and infrared absorption spectra of the liquid are obtained. Spectral simplification and number densities of impurities in the optical path are substantially higher than are obtainable in similar gas-phase analyses. Carbon dioxide impurity (~2 ppm) present in commercial Xe and ppm levels of Freon 12 and vinyl chloride added to liquefied air are used to illustrate the method.

3 Claims, 3 Drawing Figures

METHOD FOR DETECTING TRACE IMPURITIES IN GASES

BACKGROUND OF THE INVENTION

1. Field of the Invention

The invention described herein relates to a method for qualitative and quantitative determination of trace impurities in carrier gases, and more specifically to a method wherein the gas to be examined is liquefied by cooling and pressurization and brought to a temperature at which the dissolved impurities have sufficiently narrow absorption spectra to be readily distinguished from one another by ir or uv spectrometry. It is a result of a contract with the Department of Energy.

There are several methods for identifying and determining trace impurities in gases, such as mass spectroscopy, gas chromatography, and infrared spectrometry, or a combination of these methods. Infrared spectrometry has the advantage of being a versatile technique, but it suffers from poor sensitivity and occasionally from poor specificity, i.e., from difficulty in identifying overlapping bands of different compounds when complex mixtures are to be analyzed. Very long pathlengths may be employed to overcome the poor sensitivity, but with certain mixtures, quantitative and often qualitative analysis is still impossible.

In this patent application we present a method for greatly improving the sensitivity and specificity of infrared spectrometry as applied to quantitative determination of some trace impurities in gases by utilizing cryogenic solutions. Solubilities of trace gases in liquefied carrier gases are often sufficiently high to make analyses practical. Since molecular densities in liquids are $\sim 2 \times 10^{22}$ molecules/cm$^3$, a 1-ppm level of some impurity translates into $\geq 10^{16}$ molecules/cm$^3$ of impurity in solution, much above the molecular density in the gas phase. Molecular rotation is suppressed in solution, so that the generally complex rotational structure of a solute vibrational band usually collapses to a single, sharp feature having a peak absorbance (at moderate resolutions) higher than that for the gas at room temperature. Provided that the liquefied carrier gas is essentially free of infrared absorptions at wavelengths where the impurities absorb, detection of low levels (ppm-ppb) of impurities can be performed.

2. Description of the Prior Art

A careful review of the novelty search material has uncovered one patent. U.S. Pat. No. 2,917,629 (Method for the Analysis of Liquid Chlorine) teaches the investigation of impurities found in chlorine gas by infrared analysis of a liquefied sample. The method described, although superficially similar to the instant invention, has not been sufficiently investigated by the inventor to uncover its real potential. The collapse of the rotation-vibration structure is not mentioned. This spectral simplification is crucial for analysis of complicated mixtures. Further, no mention is made of the facts that the increased densities allow high sensitivity to be trivially achieved, and that the solubilities of the various impurities in the liquefied host gas determine the ultimate utility of the method. The fact that these characteristics are not claimed in this patent is either indicative that the inventor was not aware of or not interested in the possibility of generalizing the method to systems other than chlorine, and in particular that such techniques can be valuable for analyzing mixtures with complex composite features. Finally, the use of an internal mirror and other infrared light directing optics are unnecessary since the cells used for the liquefication and observation in the instant invention fit trivially into standard sample compartments in many commercially available spectrometers.

3. Statement of the Objects

An object of the invention is the demonstration that conventional spectrometry can be used to analyze trace impurities in some gases with considerably greater sensitivity and specificity than is commonly expected if the mixture is liquefied. Other objects and novel features of the invention will become apparent to those skilled in the art upon examination of the following detailed description of a preferred embodiment of the invention and the accompanying drawings.

SUMMARY OF THE INVENTION

A technique for considerably improving the sensitivity and specificity of infrared spectrometry as applied to quantitative determination of trace impurities in various carrier or solvent gases is presented. A gas to be examined for impurities is liquefied and infrared absorption spectra of the liquid are obtained. Spectral simplification and number densities of impurities in the optical path are substantially higher than are obtainable in similar gas-phase analyses. Carbon dioxide impurity ($\sim 2$ ppm) present in commercial Xe and ppm levels of Freon 12 and vinyl chloride added to liquefied air are used to illustrate the method.

DESCRIPTION OF THE PREFERRED EMBODIMENT

The invention demonstrates that conventional infrared spectrometry can be used to analyze trace impurities in some gases with improved sensitivity if the mixture is liquefied. It utilizes absorption pathlengths of the order of 1 cm, yet achieves sensitivities comparable to pathlengths of many meters under usual vapor-phase conditions. Increasing the effective pathlength by using a multiple traversal scheme or by actually lengthening the absorption cells would further improve the sensitivity of the method. The widths of the features observed in the cryogenic liquids are broader than the resolved rotational lines in low pressure gas-phase spectra but much narrower than those characteristic of high pressure. The method is illustrated in two examples. Vinyl chloride ($C_2H_3Cl$) and dichlorodifluoromethane ($CCl_2F_2$) are dissolved at ppm concentrations in liquid air, and commercially available spectroscopic grade Xe is liquefied in order to examine $CO_2$ and fluorocarbon impurities. Part-per-million levels of impurities are easily and quantitatively observable. In order to determine the approximate range of sensitivity of the technique, it was necessary to measure the peak absorption cross sections of the dissolved test gases. Two procedures for dissolution were employed. In the first, a solute gas of interest was mixed with the solvent gas and introduced into the empty, room temperature cell. The lower portion of the cell was cooled and the upper portion heated to condense the solvent gas and additive gas only in the bottom of the cell. During the condensation, a source of solvent gas was kept open to the cell. The second procedure commenced with a cell partly filled with the solvent liquid and maintained at the final temperature of interest. The premixed solute and a small amount of solvent gas were then rapidly swept into the cell with additional solvent gas and condensation was allowed to proceed until the viewing volume was filled-this point is determined by direct observation of the liquid level in the cell. In both procedures, the solution was stirred with a Teflon coated magnetic bar driven by an external source. These mixing procedures cannot put more than the measured amount of additive gas into the cell; therefore, the additive levels quoted herein are upper limits to the concentrations.

In a preferred embodiment, infrared spectra were obtained with a Perkin-Elmer Model 180 scanning spectrometer which was continuously flushed with dry nitrogen. Instrumental time constants were of the order of 2 s. The vacuum insulated, copper cryogenic cells used have been described elsewhere (Maier et al., J. Chem. Phys. 69, 1961 (1978)). Optical pathlengths and cell volumes were 1.3 cm and 2.6 cm$^3$, respectively, for the experiments conducted in liquid Xe(LXe) and 2.6 cm and 5.0 cm$^3$ for those in liquid air (LAir). Calcium fluoride windows were utilized in both cases.

Figure 1:
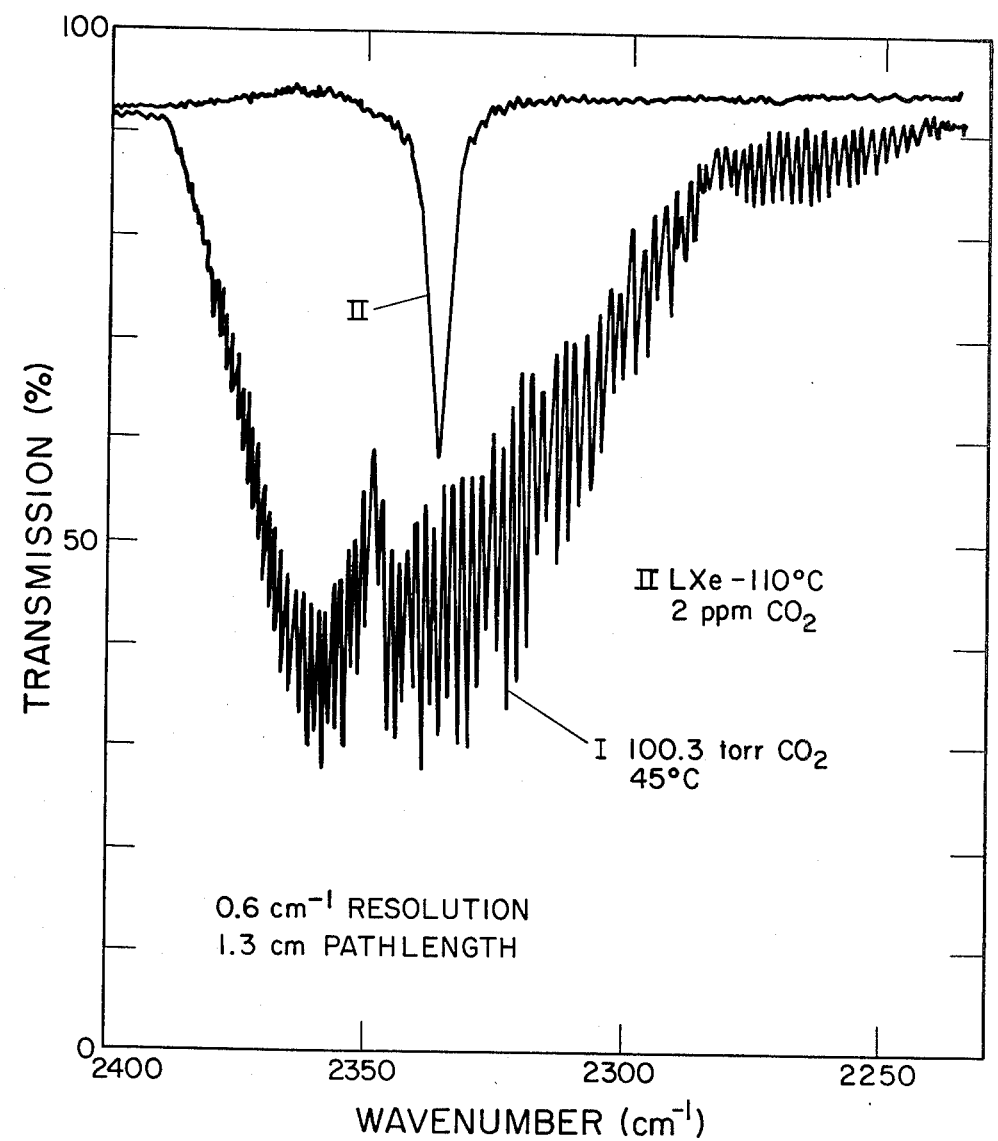
FIG. 1 is an infrared spectrum of 100.3 Torr of $CO_2$ vapor at 45° C. (Curve I) and that of 2 ppm of $CO_2$ impurity in liquid Xe at $-110°$ C. (Curve II). In the vapor, the $^{12}CO_2$ band overlaps that of $^{13}CO_2$ at the longer wavelengths.
Figure 2:
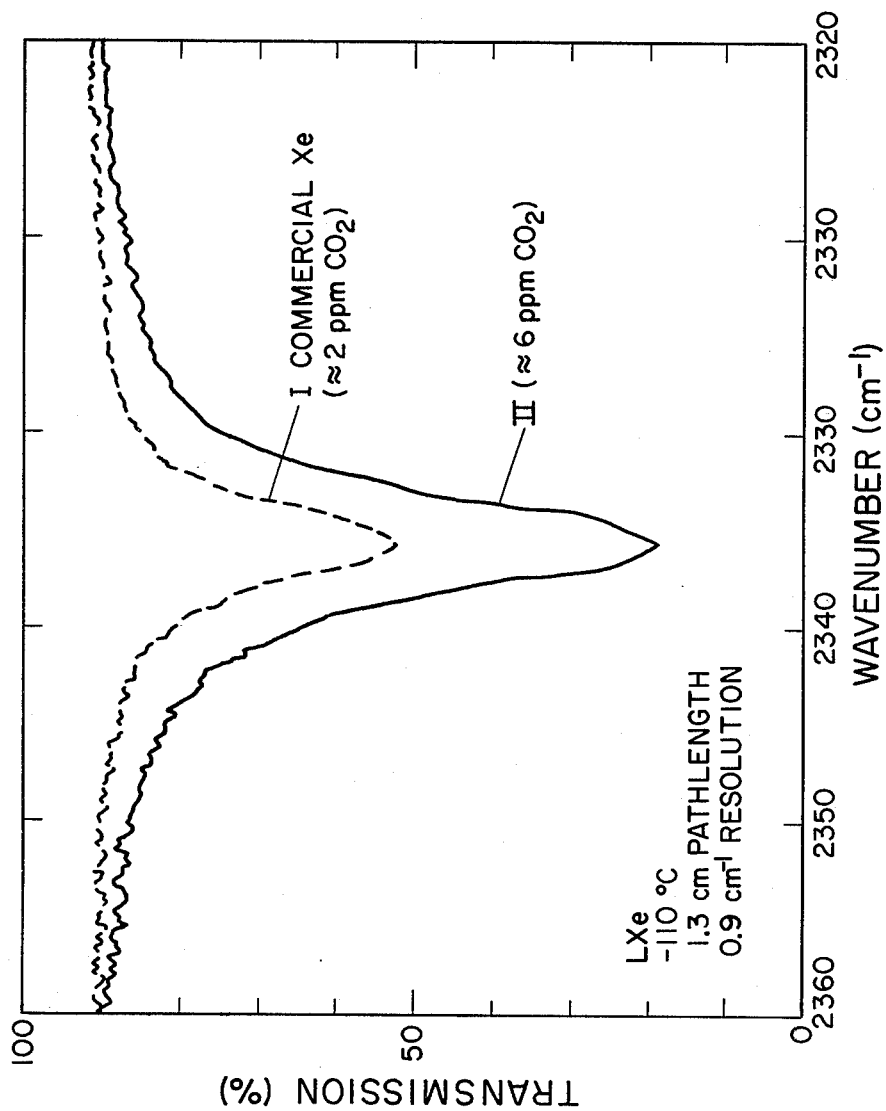
FIG. 2 is an infrared spectrum of 6 ppm total $CO_2$ dissolved in liquid Xe at $-110°$ C. (Curve I) and that of the commercial LXe used, which has about 2 ppm $CO_2$ impurity (Curve II).

The results from the $CO_2$ calibration and trace determination experiments are shown in FIGS. 1 and 2. In FIG. 1, we compare the 4-$\mu$m vapor phase spectrum of pure $CO_2$ at 45° C. with a spectrum of $CO_2$ impurity in the liquefied ($-110°$ C.) commercial spectroscopic grade xenon used in our laboratory. [Substantial ($\sim$1-100 ppm) fluorocarbon impurities have been found in samples of spectroscopic grade rare gases from several suppliers. Spectra are not given herein. The manufacturer's specifications quote <0.5 ppm $CO_2$ and levels of fluorocarbons "too low to measure".] The absorption in curve II of FIG. 1 corresponds to about 2 ppm of $CO_2$ in the xenon sample. The absorption feature of dissolved $^{13}CO_2$ in natural abundance is just perceptible at 2271 cm$^{-1}$ and corresponds to $\sim$0.02 ppm. Note the almost complete suppression of rotational structure in the liquid phase. Further, the $\nu_3$ band of the solvated $CO_2$ is broader than the individual rotational features resolved in the vapor phase spectrum, although the instrumental resolution for the two traces is identical. The width of the band in solution may be partly the result of the $CO_2$ molecules being located in a variety of environments in the liquid xenon. In other cryogenic solvents, the width of the spectral features may be different (2). Actually, the width of the $CO_2$ bands in Xe solution is convenient for quantitative analysis, since for accurate measurement of absorbance, the spectrometer pass band needs to be appreciably narrower than the spectral width of the absorption features. This requirement is easily satisfied in the solutions, with the resolutions indicated in FIGS. 1 and 2. Considerably higher resolutions than the Model 180 allows would be required to measure accurately the absorbance for the $CO_2$ gas at the pressure of FIG. 1.

FIG. 2 shows a spectral scan of approximately 6 ppm total $CO_2$ dissolved in LXe and a scan of LXe containing $CO_2$ impurity as in FIG. 1. These spectra were obtained at a slower scan speed in order to improve the quantitative determination of the peak heights. The substantial signal-to-noise ratio observed for these $CO_2$ levels suggests that a factor of 100 reduction in $CO_2$ concentration could be measured quantitatively with the same apparatus and conditions. Use of a longer optical pathlength and/or sophisticated data averaging and processing techniques would further improve the sensitivity of the method.

Figure 3:
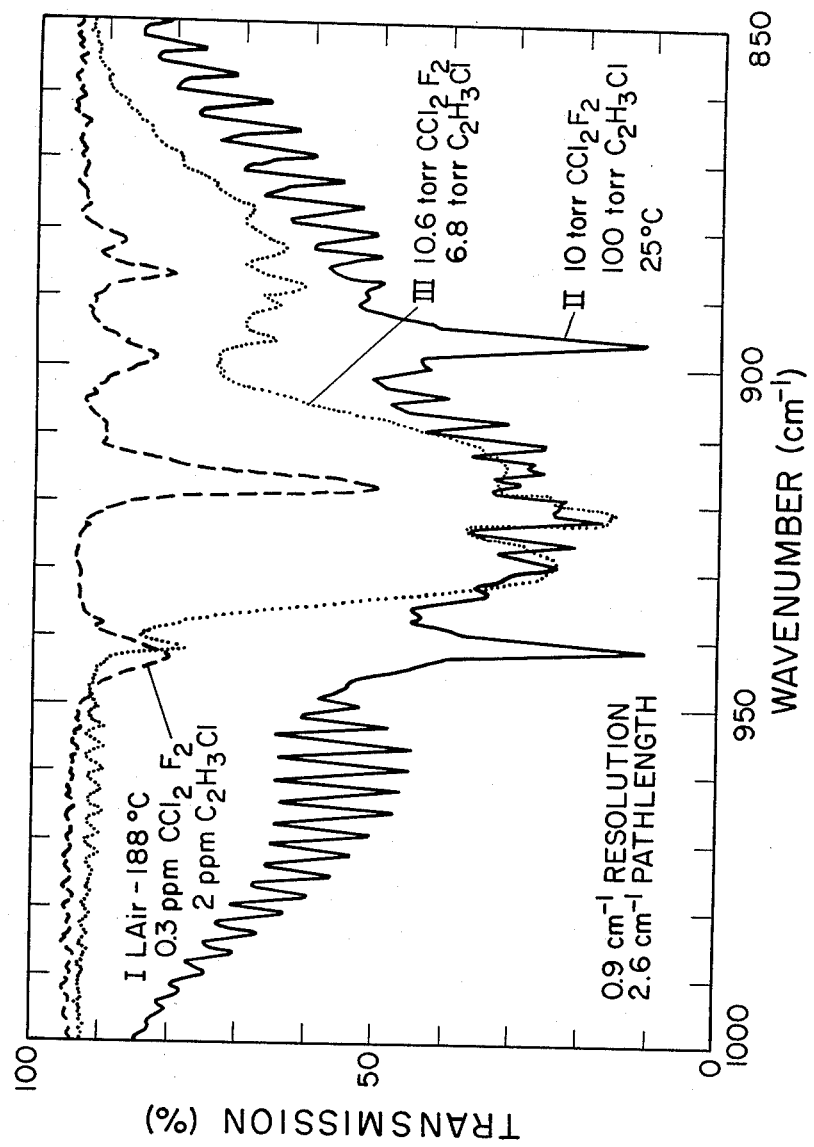
FIG. 3 is an infrared spectrum (Curve I) of the mixture of $CCl_2F_2$ (0.3 ppm; features at 917.5 and 886.5 cm$^{-1}$) and $C_2H_3Cl$ (2 ppm; features at 943.0 and 899.0 cm$^{-1}$) dissolved in liquid air at $-188°$ C., and spectra of 25° C. mixtures of 10 Torr $CCl_2F_2$ and 100 Torr of $C_2H_3Cl$ (Curve II) and 10.6 Torr of $CCl_2F_2$ and 6.8 Torr of $C_2H_3Cl$ (Curve III).

The suppression of rotational structure of solvated molecules is a general phenomenon and can be of great value in the analysis of the spectra of complex mixtures. FIG. 3 shows an infrared spectrum in the 10-$\mu$m region of a mixture of $CF_2Cl_2$ (0.3 ppm; features at 917.5 and 886.5 cm$^{-1}$) and $C_2H_3Cl$ (2 ppm; features at 943.0 and 899.0 cm$^{-1}$) dissolved in liquefied bottled air at $-188°$ C. This spectrum is compared with those for two gas-phase mixtures of the same compounds. It is apparent that little qualitative information can be derived from the vapor phase spectra, whereas the bands of the solvated molecules are completely resolved. One can test for saturated solutions by raising or lowering the temperature of the liquid and observing the effect on the absorption bands. The additive gases investigated are more soluble at higher temperatures. By maintaining a substantial pressure of solvent gas over the liquid, a broad liquid-phase temperature range is available for a given solvent.

Finally, similar experiments performed using a visible/ultraviolet spectrometer suggest that in specific cases qualitative as well as quantitative analysis can be accomplished. However, since there is no observed spectral simplication for electronic transitions, the increased specificity observed in the infrared is no longer present. The sensitivity of detection is increased over vapor phase techniques but it is not as large as that obtainable in the infrared part of the invention.

Advantages of the technique then are (a) the high densities in the optical path and the higher peak absorption cross sections provide sensitivities which are greatly improved (>10$^3$) over atmospheric pressure gas-phase methodology for similar path lengths; (b) the higher densities of the trace impurities in the liquids mean that errors due to sorption or reaction at the walls of the spectroscopic cell are not as critical as in gases, where extremely small molar concentrations are typical for trace impurities; (c) once absorptivities are known at the liquid temperature, the method gives absolute concentrations independent of the pressure of the original gaseous sample; (d) chemical reactions of species which might be unstable in the gas phase may be suppressed at the very low temperatures used; and (e) the analysis of mixtures may be facilitated by the dramatic simplification of the absorption spectra.

The foregoing description of a preferred embodiment of the invention has been presented for purposes of illustration and description and is not intended to be exhaustive or to limit the invention to the precise form disclosed. It was chosen and described in order to best explain the principles of the invention and their practical application to thereby enable others skilled in the art to best utilize the invention in various embodiments and with various modifications as are suited to the particular use contemplated. It is intended that the scope of the invention be defined by the claims appended hereto.

What is claimed is:

1. A method for qualitative and quantitative determination of trace impurities in carrier gases utilizing the solubility of vapor phase compounds in cryogenic solutions with an impurity-bearing carrier gas to be analyzed as a solvent over a range of temperatures comprising:

(a) liquefication of said impurity-bearing carrier gas at a temperature such that the absorption spectra of the dissolved impurities are sufficiently narrow to permit them to be qualitatively and quantitatively distinguished from one another without causing significant precipitation of any of the components thereby increasing the density of impurity molecules in the path of an electromagnetic interrogation beam while keeping the concentration of impurity in the carrier gas at a constant value, and (b) interrogation of said spectra in the infrared and/or ultraviolet region of the electromagnetic spectrum, away from where said carrier gas can absorb significantly.

2. The method of claim 1 wherein said interrogation is performed using infrared and/or ultraviolet spectrometers.

3. The method of claim 1 wherein said carrier gas consists of Xe or air and said impurities consist of carbon dioxide, Freon 12 and vinyl chloride.

* * * * *